(12) United States Patent
Hommeltoft

(10) Patent No.: US 6,204,425 B1
(45) Date of Patent: Mar. 20, 2001

(54) PROCESS FOR THE CATALYTIC ALKYLATION OF A HYDROCARBON FEED

(75) Inventor: Sven Ivar Hommeltoft, Hillerød (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/393,712

(22) Filed: Sep. 10, 1999

Related U.S. Application Data

(60) Provisional application No. 60/100,094, filed on Sep. 14, 1998.

(51) Int. Cl.$^7$ .................................. C07C 2/58; C07C 2/60
(52) U.S. Cl. ......................... 585/730; 585/720; 585/721
(58) Field of Search ................... 585/720, 721, 585/730

(56) References Cited

U.S. PATENT DOCUMENTS

| | | | |
|---|---|---|---|
| 3,456,033 | * | 7/1969 | Borst, Jr. . |
| 3,469,949 | * | 9/1969 | Borst, Jr. . |
| 3,501,536 | * | 3/1970 | Borst, Jr. . |
| 5,220,095 | | 6/1993 | Hommeltoft et al. ............... 585/720 |
| 5,245,100 | | 9/1993 | Hommeltoft et al. ............... 585/720 |
| 5,603,812 | | 2/1997 | Hommeltoft ............................ 203/29 |
| 5,948,240 | * | 9/1999 | Mulvaney, III et al. . |

FOREIGN PATENT DOCUMENTS 0 987 237 A2 * 3/2000 (EP) .

* cited by examiner

*Primary Examiner*—Jerry D. Johnson
(74) *Attorney, Agent, or Firm*—Ostrolenk, Faber, Gerb & Soffen, LLP

(57) ABSTRACT

Process for the alkylation of paraffinic and/or aromatic hydrocarbon feedstock with an olefinic alkylating agent by contact with a perfluorinated alkyl sulphonic acid movably adsorbed within a confined area of a fixed bed of particle contact material, wherein the fixed bed of particle contact material is subdivided in a number of elongated channels.

4 Claims, 1 Drawing Sheet

PROCESS FOR THE CATALYTIC ALKYLATION OF A HYDROCARBON FEED

This application claims the benefit of U.S. Provisional Application Ser. No. 60/100,094 filed Sep. 14, 1998.

BACKGROUND OF THE INVENTION

1. Field of the Invention

The present invention relates to an improved process for the supported liquid phase alkylation of hydrocarbon feed.

2. Description of the Related Art

Supported liquid phase alkylation is known to be carried out in a reactor with a fixed bed of appropriate particular contact material, on which a moveable reaction zone is established within a confined area of the contact material with an adsorbed perfluorinated alkyl sulphonic acid alkylation catalyst. As the alkylation reactions proceed in the reaction zone, the zone moves as a band through the reactor within the fixed bed of contact material (U.S. Pat. No 5,220,095).

The downstream portion of the reaction zone is, thereby, substantially horizontal levelled across the sectional area of the reactor during migration of the reaction zone. The upstream portion of the reaction zone is observed to migrate at different velocity on the reactor cross section and with different velocity than the downstream portion. This may result in differences in the reaction zone thickness as the zone migrates from top to bottom of the reactor. The different migration velocity may be caused by radial differences of the contact material loading density or particle size distribution.

SUMMARY OF THE INVENTION

It has now been found that the above disadvantage of the supported liquid phase alkylation process can be substantially avoided, when subdividing the fixed bed of contact material in a number of small vertical channels or by arranging within the reactor a number of parallel tubes loaded with the contact material.

The vertical channels may be established by arranging vertical plates or an elongated structure with parallel or cross-arranged plates within the fixed bed of contact material particle. Furthermore, the channels may be formed by one or more monolithic bodies with straight channels.

When carrying out the process in a number of small sized tubes arranged in the alkylation reactor, the alkylation reaction is advantageously cooled by indirect cooling with a cooling medium in indirect heat exchange with the reacting hydrocarbon feedstream inside the tubes.

A preferred cooling medium will be the reactor effluent stream usually containing a suitable amount of unconverted hydrocarbon feed which by indirect heat exchange is flashed off the effluent stream.

BRIEF DESCRIPTION OF THE DRAWINGS

In the following text the invention will be described more detailed by reference to the drawings, in which.

DETAILED DESCRIPTION OF THE PREFERRED EMBODIMENT

Figure 1:
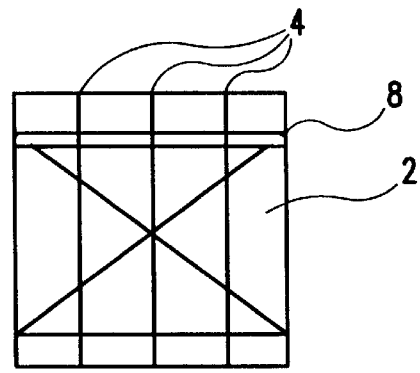
FIG. 1 is a vertical section through a reactor with a bed of particulate material divided into a number of section by means of plates according to a specific embodiment of the invention.
Figure 2:
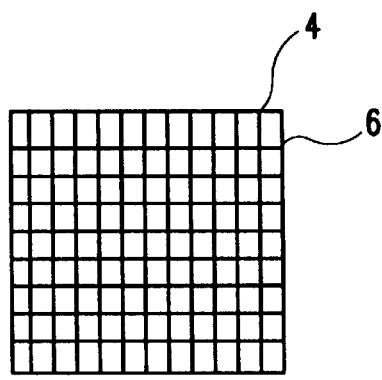
FIG. 2 is section shown horizontal through the reactor; and in FIG. 1.

In the alkylation reactor shown in FIG. 1, bed 2 with particulate contact material is subdivided into a number of small elongated departments by insertion of plates 4 and plates 6 (FIG. 2). Reaction zone 8 being adsorbed on top of bed 2, migrates then in channels between plates 4.

Figure 3:
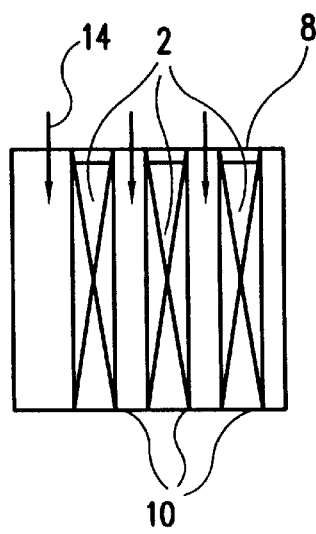
FIG. 3 shows a reactor with a number of reactor tubes being cooled indirectly with a steam of cooling agent according to a further embodiment of the invention.

FIG. 3 shows an embodiment of the invention with a number of beds 2 being arranged within tubes 10. Each bed is loaded with a moveable reaction zone 8. Reaction zone 8 is cooled by indirect heat exchange with a cooling agent 14 flowing on shell side of tubes 10 either concurrently or countercurrently with the moving reaction zone.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A process for the alkylation of paraffinic and/or aromatic hydrocarbon feedstock, comprising the steps of:

providing a fixed bed of particle contact material in a reactor body, wherein the interior of the reactor body is subdivided into a number of elongated channels each of which is filled with the particle contact material;

adsorbing a liquid catalyst within the particle contact material in each channel; and delivering the paraffinic and/or aromatic hydrocarbon feedstock into the partitioned fixed bed reactor to contact the adsorbed catalyst to produce a moving reaction zone in each channel, such that each moving reaction zone maintains a substantially uniform thickness and a substantially uniform migration velocity across the width of the respective channel.

2. The process of claim 1, wherein the fixed bed of particle contact material in the reactor body is subdivided by elongated plates positioned vertically through the bed.

3. The process of claim 1, wherein the fixed bed of particle contact material in the reactor body is subdivided by one or more monolithic straight channel bodies.

4. The process of claim 1, wherein the catalyst is perfluorinated alkyl sulphonic acid.

* * * * *